(12) United States Patent
Yu et al.

(10) Patent No.: US 8,228,187 B2
(45) Date of Patent: Jul. 24, 2012

(54) WIRELESS MONITORING DEVICE

(75) Inventors: Chu-Yih Yu, Taipei Hsien (TW); John Jiannyuh Chen, Taipei Hsien (TW)

(73) Assignee: Mesure Technology Co., Ltd., San Chung, Taipei Hsien (TW)

( * ) Notice: Subject to any disclaimer, the term of this patent is extended or adjusted under 35 U.S.C. 154(b) by 431 days.

(21) Appl. No.: 12/134,440

(22) Filed: Jun. 6, 2008

(65) Prior Publication Data

US 2009/0009319 A1    Jan. 8, 2009

(30) Foreign Application Priority Data

Jun. 8, 2007   (TW) .............................. 96209402 U

(51) Int. Cl.
*G08B 1/08* (2006.01)

(52) U.S. Cl. .............. 340/539.12; 128/204.23; 128/903; 340/573.1; 368/282; 368/283; 600/300; 600/503

(58) Field of Classification Search ............. 340/539.11, 340/539.12, 573.1; 600/490, 503
See application file for complete search history.

(56) References Cited

U.S. PATENT DOCUMENTS

| | | | | |
|---|---|---|---|---|
| 3,589,818 A * | 6/1971 | Mountain | ..................... | 356/220 |
| 5,642,733 A * | 7/1997 | Archibald et al. | ............ | 600/485 |
| 5,802,014 A * | 9/1998 | Danko | ............................. | 368/10 |
| 5,810,736 A * | 9/1998 | Pail | ................................ | 600/500 |
| 7,175,340 B1 * | 2/2007 | Kinney | .......................... | 368/282 |
| 2002/0109600 A1 * | 8/2002 | Mault et al. | ................. | 340/573.1 |
| 2002/0170359 A1 * | 11/2002 | Yamakoshi et al. | ............ | 73/756 |
| 2005/0033187 A1 * | 2/2005 | Itonaga et al. | ................ | 600/485 |
| 2006/0224047 A1 * | 10/2006 | Suzuki et al. | ................. | 600/300 |
| 2008/0007390 A1 * | 1/2008 | Wells et al. | ................. | 340/407.1 |

* cited by examiner

*Primary Examiner* — Brent Swarthout

(74) *Attorney, Agent, or Firm* — Thomas, Kayden, Horstemeyer & Risley, LLP

(57) ABSTRACT

An exemplary embodiment of a wireless monitoring device includes a sensitive patch with a sensor for sensing a body part and generating a signal. A wireless transmitter includes a first connection portion coupling to the sensitive patch for transmitting the signal. A mounting belt device is affixed to the wireless transmitter and securable in a closed loop configuration for coupling the wireless transmitter to an object. A wireless receiver is adapted for receiving the signal. The wireless receiver includes a display surface for displaying a value corresponding the signal and a supporting surface with a second connection portion. The wireless receiver and the wireless transmitter are detachably combined by coupling the first connection portion and the second connection portion, thereby keeping the wireless receiver and the wireless transmitter in an upright position.

5 Claims, 5 Drawing Sheets

WIRELESS MONITORING DEVICE

BACKGROUND OF THE INVENTION

The invention relates to the field of wireless monitoring devices. More particularly, the invention relates to the field of wireless body temperature monitoring devices.

The use of monitoring devices is known in the prior art. By way of example, U.S. Pat. Nos. 6,238,354, 5,938,618, 5,559,497 and 66,415,442 disclose remote non-invasive patient temperature monitor and warning systems.

However, the aforementioned patents do not described how to easily store a wireless monitoring device and keep it there to use later and make the patient feel comfortable. Based on the above, there is a need for medical instrumentation which is uncomplicated in its design and method of operation and which is specifically capable of being used in the home for purposes of the continuously monitoring of body temperature even while the patient is sleeping. Such improved medical instrumentation should also be capable of allowing the continuous observation of temperature data of a patient being monitored, at a remote location such that a remote unit or casing can be dimensioned and configured to be either carried on the person of, an observer or positioned or located at a convenient, readily accessible site.

SUMMARY OF THE INVENTION

An exemplary embodiment of the present invention overcomes the above-described problems by providing a wireless monitoring device, which comprises a sensitive patch, comprising a sensor for sensing a body part and generating a signal; a wireless transmitter with a first connection portion, coupling to the sensitive patch for transmitting the signal; a mounting belt device, affixed to the wireless transmitter and securable in a closed loop configuration for coupling the wireless transmitter to an object; and a wireless receiver, adapted for receiving the signal, the wireless receiver comprising a display surface for displaying a value corresponding the signal and a supporting surface with a second connection portion; wherein the wireless receiver and the wireless transmitter are detachably combined by coupling the first connection portion and the second connection portion, thereby keeping the wireless receiver and the wireless transmitter in an upright position.

Another exemplary embodiment of the present invention provides a sensitive patch, which comprises a sensor for sensing a body part and generating a signal; a contact pad with a front side surface and a back side surface, the front side surface adapted to be placed in contact with a body part, wherein an opening is formed through the front side surface thereof; and a protection layer, disposed on the back side surface of the contact pad, wherein at least a portion of the sensor is disposed in the opening and structured to directly sense the body part.

Another exemplary embodiment of the present invention provides a mounting belt device, which comprises a main strap comprising a mounting surface with a first area and a second area adjacent thereto, affixed to a portable equipment and securable in a closed loop configuration for coupling the portable equipment to an object; a first subsidiary strap, removably attached to the first area of the main strap for covering a cable extending to connect the portable equipment; and a second subsidiary strap, removably attached to the second area of the main strap.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF THE INVENTION

Various aspects of the system and method of the present invention will be described, and for purposes of explanation, specific configurations and details are set forth in order to provide a thorough understanding of the present invention. However, it will be apparent to one skilled in the art that the present invention may be practiced without these specific details. Furthermore, well known features have been omitted or simplified in order to prevent obscuring the present invention.

Figure 1:
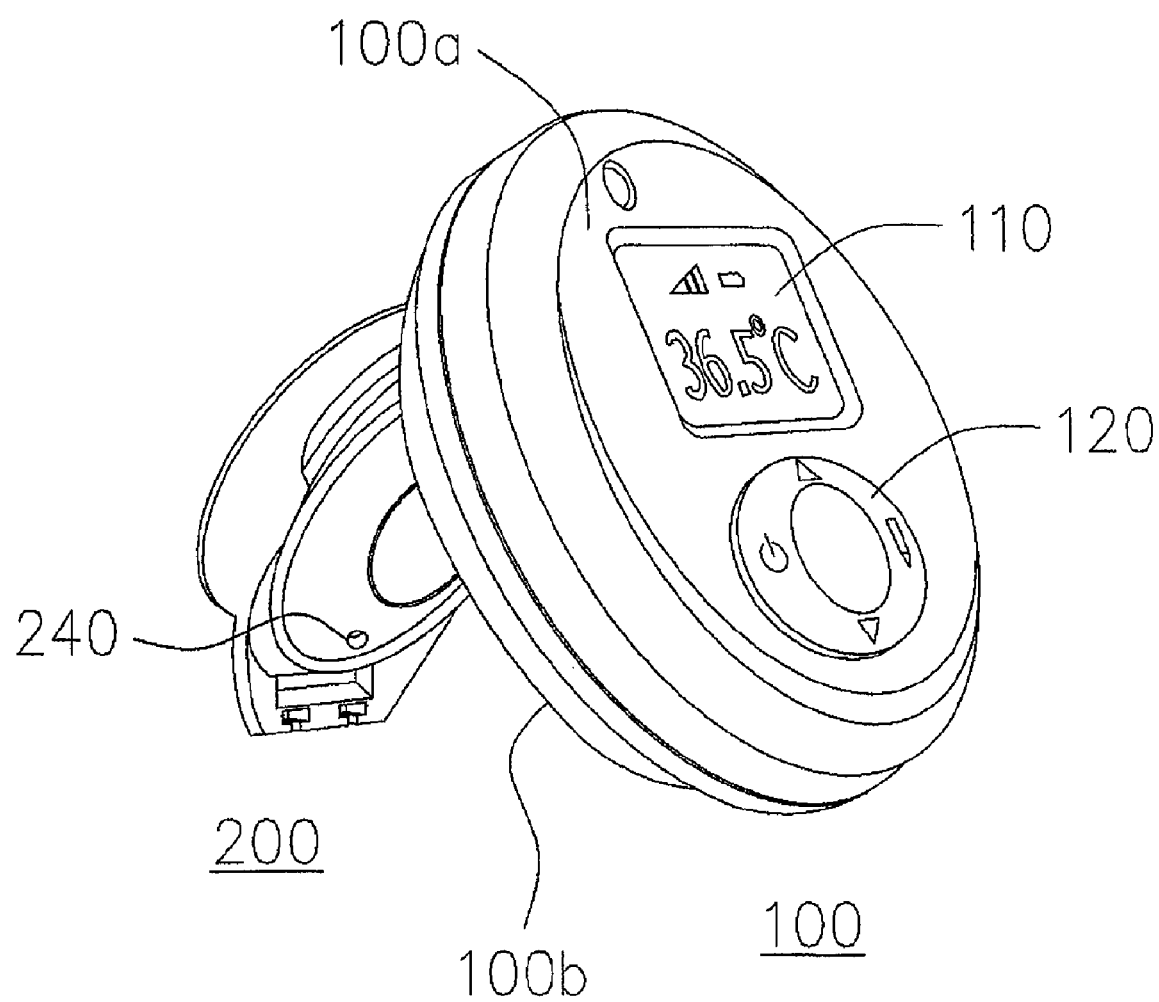
FIGS. 1-3 are schematic illustrations of a wireless monitoring device according to an exemplary embodiment of the present invention.
Figure 2:
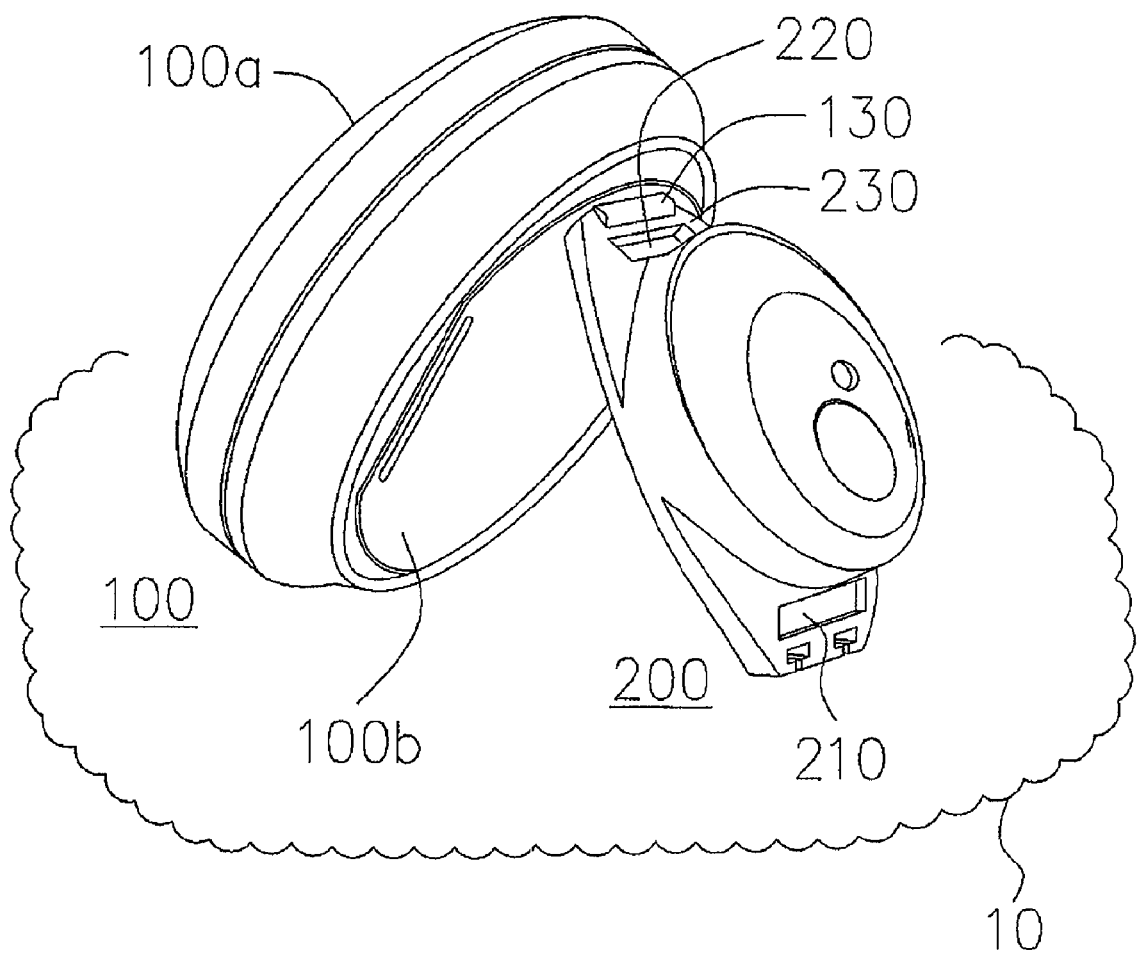
Figure 3:
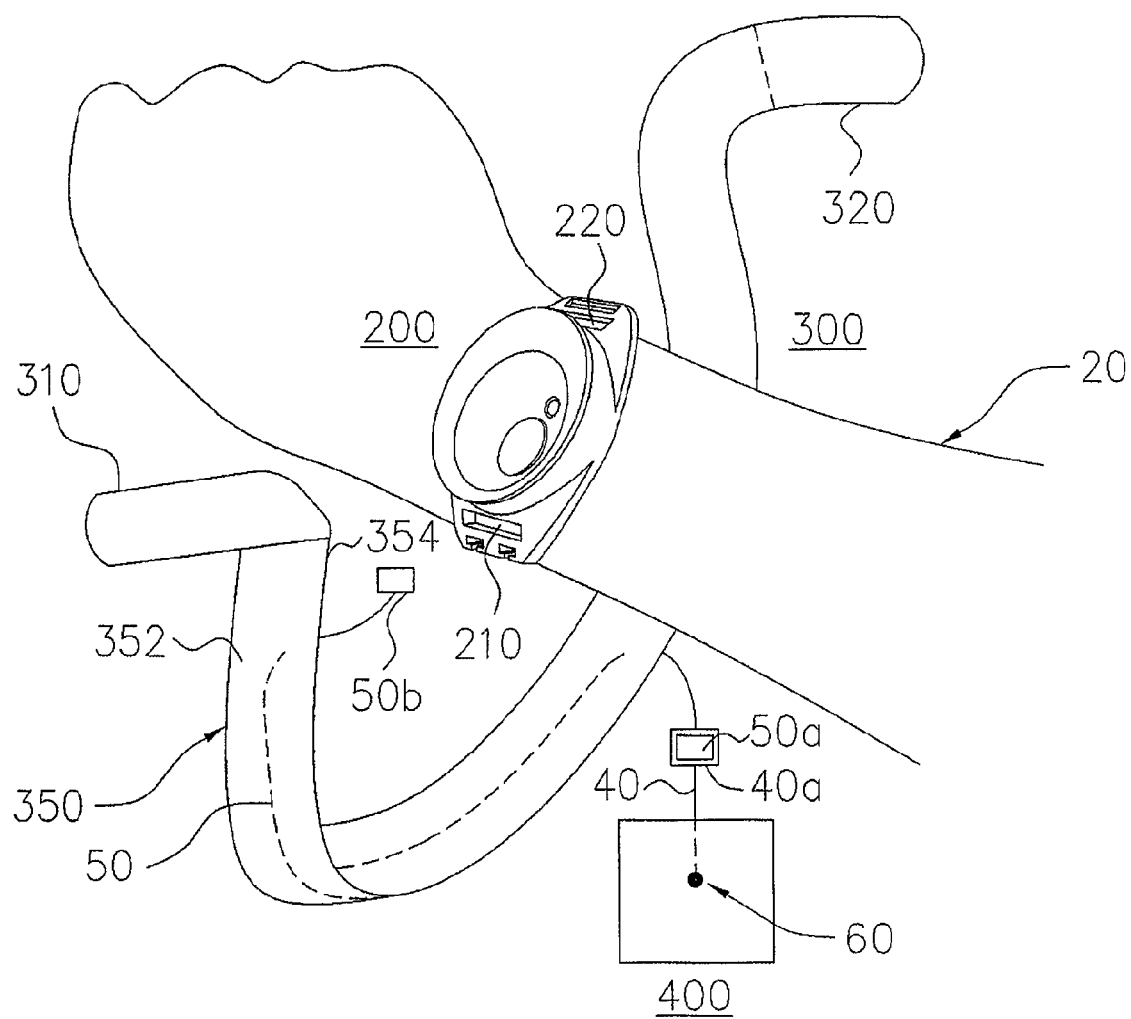

Referring to FIGS. 1-3, an exemplary embodiment of a wireless monitoring device includes a sensitive patch 400 with a sensor 60 for sensing a user's body part and generating a signal. A wireless transmitter 200 coupling to the sensitive patch 400 for transmitting the signal includes a first connection portion 230. A mounting belt device 300 is affixed to the wireless transmitter 200 and securable in a closed loop configuration for coupling the wireless transmitter 200 to an object, such as the wrist, arm, or other portions of the user's body.

A wireless receiver 100 is adapted for receiving the signal. The wireless receiver 100 includes a display surface 100a for displaying a value corresponding the signal and a supporting surface 100b with a second connection portion 130. The wireless receiver 100 and the wireless transmitter 200 are detachably combined by coupling the first connection portion 230 and the second connection portion 130, thereby keeping the wireless receiver 100 and the wireless transmitter 200 in an upright position. That is, it is easily to store the wireless monitoring device and keep it standing on a platform 10 to use later. In this situation, the wireless receiver 100 can serve as a thermometer, clock or time counter.

In one example, display surface 100a comprises a display assembly 110 which is employed to display a value corresponding the signal received by the receiver 100. A control switch 120 disposed on the display surface 100a is capable of turning on or off the display assembly 110.

Figure 4:
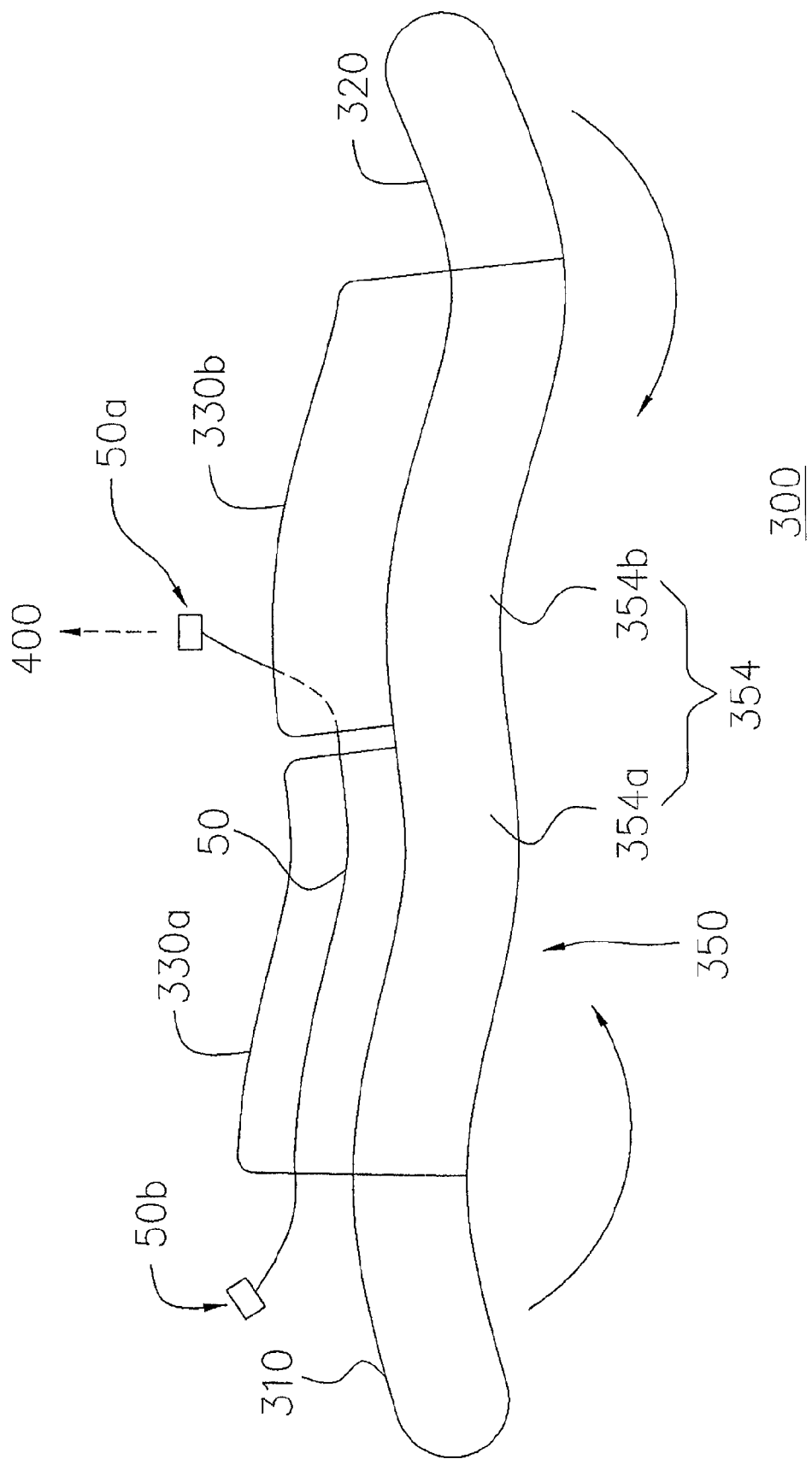
FIG. 4 is a schematic illustration of a mounting belt device according to an exemplary embodiment of the present invention.

For example, turning now to FIG. 4, mounting belt device 300 may comprise a main strap 350. In general, the main strap 350 comprises a mounting surface 354 with a first area 354a and a second area 354b adjacent to the first area 354a. Specifically, referring to FIG. 3, mounting surface 354 is affixed to a portable equipment, such as wireless transmitter 200, and securable in a closed loop configuration for coupling the portable equipment to an object, generally, the wrist of patient.

The mounting belt device 300 further comprises a first subsidiary strap 330a, which is removably attached to the first area 354a of the main strap 350 for covering a cable 50. In an exemplary embodiment, one end of the cable 50 is extended to connect the portable equipment. For example, The end of the cable 50 may couple to the wireless transmitter 200 through a connection 50b. And then, the connection 50b can be inserted into a hole 240 of the wireless transmitter 200 for transmitting the signal.

Yet another feature of the mounting belt device 300 is the provision of a second subsidiary strap 330b, which is removably attached to the second area 354b of the main strap 354. In this embodiment, the cable 50 is not covered by the second subsidiary strap 330b. However, the second subsidiary strap 330b may be used instead of the first subsidiary strap 330a to cover the cable 50 while the first subsidiary strap 330a is failed or easily loosed, since the straps 330a and 330b are removable. Thus, the lifetime of the mounting belt device 300 could be extended longer than before.

On the other hand, the first subsidiary strap 330a and the second subsidiary strap 330b may have the same thickness. That is, the first subsidiary strap 330a covering cable 50 and the second subsidiary strap 330b without covering the cable may construct a planar surface. And thus the patient would feel more comfortable when the mounting surface 354 with the two subsidiary strap 330a and 330b to be attached to the user's body.

Figure 5:
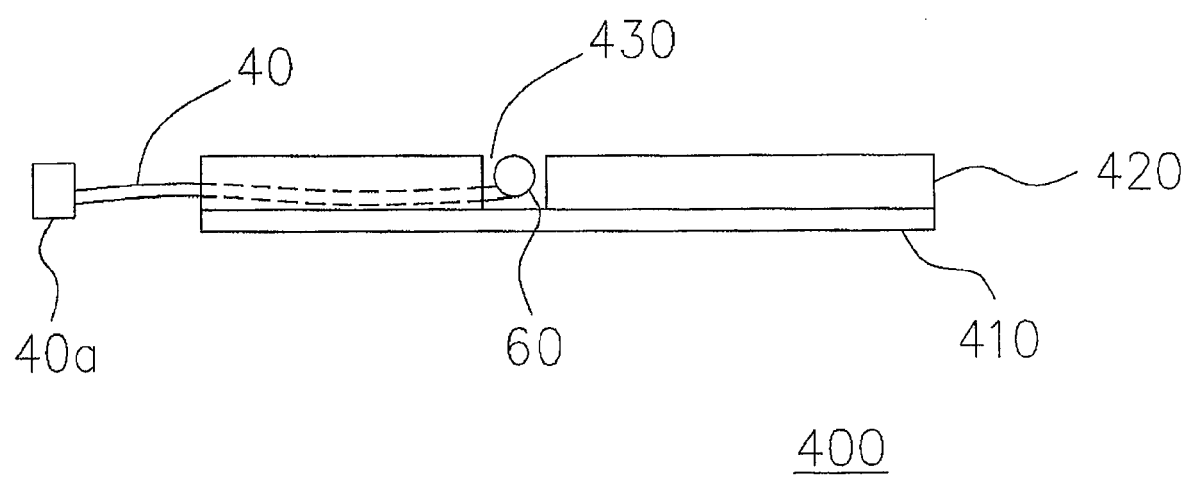
FIG. 5 is a schematic illustration of a sensitive patch according to an exemplary embodiment of the present invention.

Looking now to FIG. 5, the sensitive patch 400 comprises a sensor 60 for sensing a body part and generating a signal. The sensor may be employed to sense the patient's temperature, blood pressure, pulse, or body fat. In a preferred embodiment, the sensitive patch 400 comprises a contact pad 420 with a front side surface and a back side surface. Specifically, the front side surface is placed in contact with the body part, in which an opening 430 is formed through the front side surface thereof. Further, a protection layer 410 is disposed on the back side surface of the contact pad 420. A feature in the embodiment is that at least a portion of the sensor 60 is disposed in the opening 430 and structured to directly sense the body part and generate the signal. In one example, the sensor 60 and the opening 430 may have a substantial coplanar plane. Thus, the patient would feel more comfortable when the sensor 60 is attached to the user's body. A cable 40 sandwiched between the contact pad 420 and the protection layer 410 is extended from the sensor 60 to a connection 40a.

Turning now to FIGS. 3-4, the connection 40a is inserted into a connection 50a which connects another end of the cable 50 to transmit the signal. Typically, the cable 50 may enter into a space between the subsidiary strap 330a and the main strap 350 through a gap between the two subsidiary straps 330a and 330b. In one example, the straps may be dimensioned and configured to be removably attached to a patient, such as about the wrist, arm or other portions of the user's body. The illustrated strap 350 may comprise a first and second removably attachable, connector components 310 and 320 which are inserted into holes 210 and 220 of the wireless transmitter 200. The connector components 310 and 320 are preferably, but not necessarily, in the form of a hook and loop type fastener. Naturally, other type of connector components may be utilized such as a buckle, snap-type connectors, tie, draw string, adhesive, etc.

While the invention has been described by way of example and in terms of the preferred embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A wireless monitoring device, comprising:
   a sensitive patch, comprising a sensor for sensing a body part and generating a signal;
   a wireless transmitter with a first connection portion, coupling to the sensitive patch for transmitting the signal;
   a mounting belt device, affixed to the wireless transmitter and securable in a closed loop configuration for coupling the wireless transmitter to an object; and
   a wireless receiver, adapted for receiving the signal, the wireless receiver comprising a display surface for displaying a value corresponding the signal and a supporting surface with a second connection portion;
   wherein the wireless receiver and the wireless transmitter are detachably combined by coupling the first connection portion and the second connection portion at upper ends of the wireless receiver and the wireless transmitter, and lower ends thereof are separated by a distance to keep the wireless receiver and the wireless transmitter standing on a platform for store; and
   wherein the mounting belt device further comprises:
   a main strap comprising a mounting surface with a first area and a second area adjacent thereto;
   a first subsidiary strap, removably attached to the first area of the main strap for covering a cable extending to connect the wireless transmitter; and
   a second subsidiary strap, removably attached to the second area of the main strap, wherein the cable is not covered by the second subsidiary strap while the first subsidiary strap is normal and is covered by the second subsidiary strap while the first subsidiary strap is failed or easily loosed.

2. The wireless monitoring device as recited in claim 1 wherein the sensitive patch further comprises:
   a contact pad with a front side surface and a back side surface, the front side surface adapted to be placed in contact with the body part, wherein an opening is formed through the front side surface thereof; and
   a protection layer, disposed on the back side surface of the contact pad, wherein at least a portion of the sensor is disposed in the opening and structured to directly sense the body part and generate the signal.

3. The wireless monitoring device as recited in claim 1 wherein the sensor and the opening have a substantial coplanar plane.

4. The wireless monitoring device as recited in claim 1, the cable further extending to connect the sensitive patch for transmitting the signal to the wireless transmitter.

5. The wireless monitoring device as recited in claim 1, wherein the first subsidiary strap and the second subsidiary strap have the same thickness.

\* \* \* \* \*